United States Patent [19]

Kämmerer et al.

[11] 4,258,046

[45] Mar. 24, 1981

[54] PYRANO-HETEROCYCLES AND MEDICAMENTS CONTAINING THESE COMPOUNDS

[75] Inventors: Friedrich-Johannes Kämmerer, Hochheim am Main; Ulrich Gebert, Kelkheim; Hans G. Alpermann, Königstein, all of Fed. Rep. of Germany

[73] Assignee: Hoechst Aktiengesellschaft, Frankfurt am Main, Fed. Rep. of Germany

[21] Appl. No.: 68,679

[22] Filed: Aug. 22, 1979

[30] Foreign Application Priority Data

Aug. 21, 1978 [DE] Fed. Rep. of Germany ....... 2836470

[51] Int. Cl.³ ............... C07D 491/06; C07D 491/052; A61K 31/47
[52] U.S. Cl. ..................................... 424/258; 546/62; 546/92
[58] Field of Search .................. 546/89, 92, 66, 92, 546/62; 424/258, 262, 258

[56] References Cited

PUBLICATIONS

Bowman et al., J. Chem. Soc. 444–447, 1959.
Storer et al., Tetrahydron 29, 1721–1723, 1973.
Venturella et al., Gazz. Chim. et al., 104, 297–307, 1974.
Noehammer et al., Chem. Abst., vol. 86, 155477k.
Nair. Chem. Abst., vol. 74, 111944h.
Chem. Abst. vol. 88, 4351cs.
Ziegler et al., Mh. Chem. 90, 762–767, (1959), 92, 927–934, (1961).
Chemical Abstracts, 8th Coll., p. 437 and p. 26288.

*Primary Examiner*—John D. Randolph
*Assistant Examiner*—Jane T. Fan
*Attorney, Agent, or Firm*—Curtis, Morris & Safford

[57] ABSTRACT

Pyrano-heterocycles of the formula

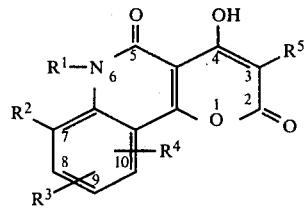

in which $R^1$ represent hydrogen or an alkyl radical containing up to 4 carbon atoms; $R^2$ represents hydrogen or an alkyl, alkoxy or haloalkyl radical each having up to 3 carbon atoms, or halogen; or $R^1$ and $R^2$ together form an ethylene or propylene group, and $R^3$ and $R^4$, independently of each other, are hydrogen or alkyl or alkoxy radicals each of which groups containing up to 3 carbon atoms, which may be unsubstituted or substituted totally or partially with halogen atoms, halogen or alkoxycarbonyl having up to 3 carbon atoms in the alkyl group and $R^5$ represents a nitro group or hydrogen, their physiologically tolerated salts, processes for preparing these compounds and medicaments containing these compounds.

5 Claims, No Drawings

PYRANO-HETEROCYCLES AND MEDICAMENTS CONTAINING THESE COMPOUNDS

The cyclization of anilines and of tetrahydroquinoline with activated malonic acid derivatives in a ratio of 1:2 under formation of pyrano-quinolines or of the pyrano-benzoquinolizinone has already been described in the literature (literature citations follow formula IIa).

Now, we have found that compounds with valuable pharmacological properties are obtained by introducing an additional nitro group into the pyrano ring. Such compounds are active against certain immuno-reaction diseases, in particular against immediate hypersensitivity reactions (anaphylaxis). Furthermore, they are distinguished by a strong systemic antiallergic action and, therefore, they are suitable for the treatment and/or the prophylaxis of allergy diseases.

Thus the object of the present invention are pyrano-heterocycles of the formula Ia

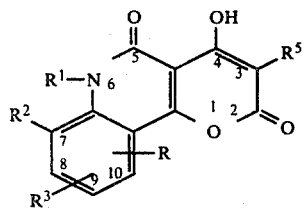

in which $R^1$ represents hydrogen or an alkyl group having up to 4 carbon atoms, $R^2$ represents hydrogen, alkyl, alkoxy or haloalkyl, each of the latter groups having up to 3 carbon atoms, or halogen (halogen being either fluorine, chlorine or bromine), or $R^1$ and $R^2$ together form an ethylene or propylene group, and $R^3$ and $R^4$, independently of each other, represent hydrogen, alkyl or alkoxy groups each of which having up to 3 carbon atoms and which may be unsubstituted or substituted, totally or partially, with identical or different halogen atoms (for example, fluorine, chlorine or bromine), halogen (fluorine, chlorine, bromine or iodine), alkoxycarbonyl of up to 3 carbon atoms in the alkyl group, and $R^5$ represents the nitro group or hydrogen, but under the proviso that—if $R^5$ is hydrogen—

(a) one of the radicals $R^3$ and $R^4$ is different from hydrogen if $R^1$ and $R^2$ together represent a propylene group, (b) $R^1$ is different from hydrogen and methyl, if $R^2$, $R^3$ and $R^4$ represent at the same time hydrogen, and (c) $R^2$ represents a substituent other than methoxy, if $R^1$ and $R^3$ represent hydrogen and $R^4$ represents methoxy in the 8- or 9-position, and the physiologically tolerated salts of these compounds, preferably the alkali metal salts, the alkaline earth metal salts as well as the ammonium salts including those of organic bases.

Compounds of the formula I

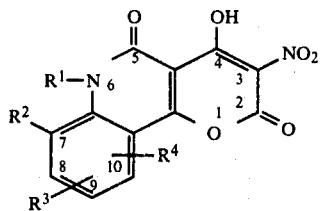

and their salts, in which $R^1$ and $R^2$ together form a propylene group, and $R^3$ and $R^4$, which may be identical or different, represent hydrogen, alkyl or alkoxy groups each of these groups having up to 2 carbon atoms, or halogen (such as fluorine, chlorine or bromine) or the $CF_3$-group, are preferred.

Furthermore, compounds of the formula I and their salts are preferred in which $R^1$ represents hydrogen or alkyl having up to 3 carbon atoms, $R^2$ represents hydrogen, and $R^3$ and $R^4$, which may be identical or different, represent hydrogen, alkyl or alkoxy groups, each of these groups having up to 2 carbon atoms, alkoxycarbonyl containing up to 3 carbon atoms in the alkyl group, halogen (such as fluorine, chlorine or bromine), or the $CF_3$-group.

The invention also includes the tautomeric structures of the compounds of the formula I.

The invention furthermore relates to a process for preparing the compounds of the formula I and their salts, in which $R^1$ represents hydrogen or alkyl having up to 4 carbon atoms, $R^2$ represents hydrogen, alkyl, alkoxy or haloalkyl, each of these groups containing up to 3 carbon atoms, or halogen, or $R^1$ and $R^2$ together form an ethylene or propylene group, and $R^3$ and $R^4$, independently of each other, are hydrogen, alkyl or alkoxy groups each of which groups having up to 3 carbon atoms, which groups may be unsubstituted or substituted, totally or partially, by identical or different halogen atoms, halogen, alkoxycarbonyl having up to 3 carbon atoms in the alkyl group, which comprises nitrating the pyrano-compound of the formula II

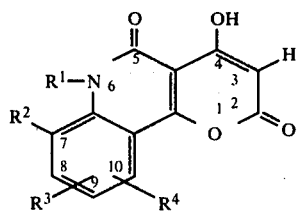

condensed with a heterocycle and in which $R^1$, $R^2$, $R^3$ and $R^4$ have the meanings given above, and optionally converting the nitro compound so obtained with bases into their physiologically tolerated alkali metal salts, alkaline earth metal salts or ammonium salts.

Basic reagents which are suitable for the salt formation are, for example, alkali metal or alkaline earth metal hydroxides, hydrides, alcoholates, carbonates and hydrogencarbonates as well as specific organic bases such as ethanolamine, diethanolamine, tris-(hydroxymethyl)-aminomethane and N-methylglucamine.

The nitration is suitably carried out in substance or in a dispersing agent or solvent which is inert toward the reaction partners under the reactions conditions. For example, acetic acid or halogenated hydrocarbons such as chloroform or carbon tetrachloride may be used for this purpose. As nitrating agent, for example the nitrous gases formed upon reaction of arsenic oxide with concentrated nitric acid, a mixture of concentrated nitric acid and acetic acid and fuming or concentrated nitric acid may be used. The nitration with a mixture of concentrated nitric acid and glacial acetic acid in a ratio of 1:1 to 1:6, preferably 1:2 to 1:3, at a temperature in the range of from 0° to 110° C., preferably from 25° to 95° C., is preferred. The reaction times are generally between a few minutes and up to two hours.

The starting products for the nitration are valuable intermediate products. They are novel, with the exception of the following compounds of the formula IIa described in the literature

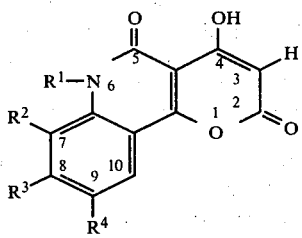

in which $R^1$, $R^2$, $R^3$ and $R^4$ represent hydrogen (E. Ziegler and H. Junek, Mh. Chem. 90, 762–767 (1959)), $R^1$ represents methyl, $R^2$, $R^3$ and $R^4$ represent hydrogen (R. E. Bowman, A. Campbell and E. M. Tanner, J. Chem. Soc. 444–447 (1959)), $R^1$ and $R^4$ represent hydrogen, $R^2$ und $R^3$ represent methoxy (R. Storer, D. W. Young, D. R. Taylor and J. M. Warner, Tetrahydron 29, 1721–1723 (1973)), $R^1$ and $R^3$ represent hydrogen, $R^2$ and $R^4$ represent methoxy (P. Venturella, A. Bellino and F. Piozzi, Gazz. Chim. Ital. 104, 297–307 (1974)) and $R^1$ and $R^2$ together represent propylene and $R^3$ and $R^4$ represent hydrogen (E. Ziegler, H. Junek and H. Biemann, Mh. Chem. 92, 927–934 (1961)).

Thus, another object of the invention are compounds of the formula II

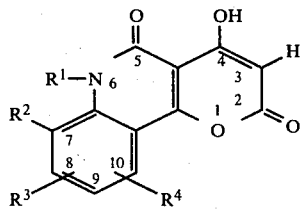

with the exception of the compounds of the formula IIa described in literature, in which $R^1$, $R^2$, $R^3$ and $R^4$ have the meanings given for the general formula I, however under the proviso that (a) one of the radicals $R^3$ and $R^4$ is different from hydrogen, if $R^1$ and $R^2$ together represent a propylene group, (b) $R^1$ is different from hydrogen and methyl, if $R^2$, $R^3$ and $R^4$ are at the same time hydrogen, and (c) $R^2$ is a substituent other than methoxy, if in formula IIa $R^3$ or $R^4$ is methoxy and the other two radicals represent hydrogen.

The starting compounds of the formula II can be prepared by reacting an amine of the formula III

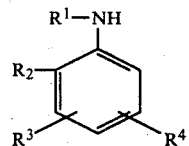

in which $R^1$, $R^2$, $R^3$ and $R^4$ have the meanings given for the general formula I, with at least double the molar quantity of a malonic acid derivative of the formula R'OOC—CH$_2$—COOR' (IV), in which R' is an alkyl radical having up to 3 carbon atoms or a phenyl radical optionally substituted up to five times by chlorine and/or bromine.

The reaction is suitably carried out in substance or in a dispersing agent or solvent which is inert toward the reaction partners under the reaction conditions. For this purpose, there may be used, for example, hydrocarbons such as tetrahydronaphthalene, decahydronaphthalene, naphthalene and paraffins, but also chloro- or bromobenzene. An excess of malonic acid derivatives of the formula IV may also be used as the reaction medium.

The compounds of the formula II are tricyclic, or if $R^1$ and $R^2$ together form an ethylene or propylene group, tetracyclic. In this case the carbon atoms of the ethylene and propylene group are counted as 7, 8 or 9 in the ring system.

A preferred process for the preparation of the tetracyclic compounds of the formula II, in which $R^1$ and $R^2$ together form an alkylene bridge, is the reaction of a tetrahydroquinoline or indoline of the formula III with the malonic acid-diethyl- or bis-2,4-dichlorophenyl ester, preferably without dispersing agent or solvent, at temperatures of between 150° and 230° C., preferably 190° and 220° C. In general, the reaction times are between a few minutes to up to 20 hours, preferably up to 10 hours. But, depending on the size of the batch, the reaction time may be longer.

A preferred process for the preparation of the tricyclic compounds of the formula II is the reaction of an aniline of the formula III with malonic acid-bis-2,4-dichlorophenyl ester in the presence of a solvent or dispersing agent which is inert toward the reaction partners under the reaction conditions, preferably in bromobenzene or tetrahydronaphthalene, at temperatures between 150° C. and the boiling point of the respective reaction mixture, preferably between 180° C. and 220° C. The reaction times are, generally, between a few minutes and up to three hours.

In particular, there may be used as the substituent $R^1$: hydrogen, methyl, ethyl, n- or isopropyl and n-, iso- or tert. butyl, $R^1$ is preferably alkyl containing 1 to 3 carbon atoms. As the substituents $R^2$, there may be used the same groups insofar as they contain up to 3 carbon atoms. $R^2$ may also be, for example methoxy, ethoxy, propoxy, trifluoromethyl, dichloromethyl, 2,2,2-trichloroethyl, chlorodifluoromethyl. Preferably, however, $R^2$ represents hydrogen, methyl or ethyl. Moreover, $R^1$ and $R^2$ may of course form together, as already indicated above, an ethylene- or propylene-group.

The substituents $R^3$ and $R^4$ may be, for example, hydrogen, methyl, ethyl, n- or iso-propyl, fluorine, chlorine, bromine, iodine, trifluoromethyl, dichloromethyl, 2,2,2-trichloroethyl, chlorodifluoromethyl, methoxy, ethoxy, trifluoromethoxy, propoxy, methoxycarbonyl, ethoxycarbonyl, propoxycarbonyl, the group CHClF—CF$_2$—O—, the alkyl, alkoxy, haloalkyl-, haloalkoxy and alkoxycarbonyl radicals preferably having up to 2 carbon atoms. Preferably, one of these radicals is different from hydrogen. As compounds in which $R^3$ as well as $R^4$ are not hydrogen, there may be used the dihalogeno compounds such as the dichloro- and dibromo-compounds, the monohalogeno-monoalkyl- or -monoalkoxy- or monohaloalkyl-compounds and the chloromethyl-, chloromethoxy- and chlorotrifluoromethyl-compounds may be used.

The novel compounds of the formula II are listed in Table 1.

The nitro compounds of the present invention of the general formula I and their physiollgically tolerable salts may be used as medicaments owing to their pharmacological properties, either alone, for example in the form of microcapsules, or in admixture with suitable carriers.

Accordingly, the invention also relates to medicaments which comprise at least one compound of the formula I, optionally in the form of one of its physiologically tolerated salts or this active ingredient in admixture with pharmaceutically acceptable carriers and/or diluents. These compositions can be administered orally, rectally or parenterally, the oral administration being preferred. Adult patients suffering from allergic reactions are treated with dosage units containing from 10 to 500 mg of a compound of the formula I normally up to three times a day. Dosage units of 50 to 300 mg are preferred. The inhalation of finely distributed powder is a possible form of administration. Suitable solid or liquid galenic preparations are, for example, granules, powders, tablets, capsules, suppositories, syrups, emulsions, suspensions, drops or injectable solutions as well as preparations with protracted release of the active principle. Frequently used carriers are, for example, magnesium carbonate, various kinds of sugar or starch, cellulose derivative, gelatin, oils of animal and plant origin, polyethylene glycols and solvents.

A special application of the compounds of the formula I and of their salts is the combination with other suitable active substances, for example with bronchospasmolytic and antihistaminic agents.

The novel products of the formula I and their alkali metal or ammonium salts are listed in Table 2. The ratio data in the examples are always referred to the volume.

EXAMPLES (1a)
11-Chloro-7,8-dihydro-2,5-dioxo-2H,5H,9H-benzo[ij]-pyrano[2,3-b]quinolizine-4-ol of the formula II 1 Mol of 6-chloro-1,2,3,4-tetrahydroquinoline of the formula III (167.6 g) and 2 moles of malonic acid-bis-2,4-dichloro-phenyl ester (788.1 g) are heated for 15 minutes under reflux (about 220° C.). After cooling of the reaction mixture, the 2,4-dichlorophenol is distilled off under reduced pressure in a rotary evaporator. The crystalline magma which is remaining is dissolved in hot tetrahydrofurane and the crystalline precipitate formed after cooling of the solution is filtered off with suction, washed with isopropanol and dried. 185.3 g (61% of the theory) of crystals are obtained; melting point after recrystallization from dioxane: 283° to 287° C. (decomp).

(1b)

The same compound is obtained by reaction of the above tetrahydroquinoline with a least 2 moles of malonic acid diethyl ester.

0.1 Mol 6-chloro-1,2,3,4-tetrahydroquinoline of the formula III (16.8 g) and 0.7 mole of malonic acid diethyl ester (112.1 g) are heated to the boil, while stirring, and the ethanol formed during this time is distilled off. The inner temperature of the mixture is raised to 200° to 202° C. in such a slow manner that the reaction is proceeding while only ethanol is distilled off. When the reaction is terminated, the mixture is allowed to cool, the crystal magma is filtered off with suction and washed with ethanol and petroleum ether.

After drying, 27.5 g (90.5% of the theory) of crystals are obtained; melting point after recrystallization from dioxane: 283° to 287° C. (decomp.). When using 0.22 mole of malonic acid diethyl ester, 22.7 g (74.9% of the theory) of a crystalline product are obtained; melting point (after recrystallization from dioxane: 283° to 287° C. (decomp.).

2.
6-Ethyl-8-chloro-5,6-dihydro-2,5-dioxo-2H-pyrano[3,2-c]-quinoline-4-ol of the formula II 0.5 Mol N-ethyl-3-chloroaniline of the formula III (77.8 g) and 1 mole malonic acid bis-2,4-dichlorophenyl ester (394.1 g) are heated for 15 minutes under reflux in 150 ml tetrahydronaphthalene (about 210° C.). 3 g of active charcoal are added to the reaction solution and the latter is stirred for 10 minutes at 190° to 200° C. It is then filtered and the filtrate is concentrated to dryness under reduced pressure in a rotary evaporator. The oily residue (90.5 g) which contains many crystals, is boiled with 2 l of n-butanol. Thereby, one part of the residue is dissolved. Then, the whole is filtered while hot. The filter residue is washed first with isopropanol and then with petroleum ether and dried. 59.2 g (40.6% of the theory) of a crystalline powder are obtained; melting point (after recrystallization from n-butanol) 276°-278° C. The n-butanol phase is allowed to stand over night at 5° C. The crystalline precipitate formed is filtered off with suction, washed and dried. Further 23.6 g (16.2% of the theory) of the crystalline powder having a melting point of 276°-278° C. (after recrystallization from n-butanol) are so obtained. In the whole, 82.8 g (56.8% of the theory) of crystalline powder are obtained which has a melting point of 276°-278° C. (after recrystallization from n-butanol).

The compounds obtained in a manner analogous to that described in the above examples are listed in the following Table 1.

TABLE 1

| | Compounds of the formula II | | | | |
|---|---|---|---|---|---|
| Ex. | $R^1$ | $R^2$ | $R^3$ | $R^4$ | melting point °C. |
| 1 | —CH$_2$—CH$_2$—CH$_2$— | | H | 11-Cl | 283–287 (decomp.) |
| 2 | —C$_2$H$_5$ | H | 8-Cl | H | 276–278 |
| 3 | —CH$_2$—CH$_2$—CH$_2$— | | H | 11-CH$_3$ | 274–277 (decomp.) |
| 4 | —CH$_2$—CH$_2$—CH$_2$— | | H | 11-O—CH$_3$ | 296–301 |
| 5 | —CH$_2$—CH$_2$—CH$_2$ | | 11-Cl | 12-Cl | >300 |

TABLE 1-continued

| | Compounds of the formula II | | | | |
|---|---|---|---|---|---|
| Ex. | $R^1$ | $R^2$ | $R^3$ | $R^4$ | melting point °C. |
| 6 | —$C_2H_5$ | H | H | 9-Cl | (decomp.) 239–245 |
| 7 | —$CH_3$ | H | H | 9-Cl | 282–286 |
| 8 | —$C_2H_5$ | H | H | 9-F | 214–216 |
| 9 | —$C_2H_5$ | H | H | 9-$CF_3$ | 208–212 |
| 10 | —$C_2H_5$ | H | H | 9-$CO_2C_2H_5$ | 221–225 |
| 11 | —$C_2H_5$ | H | 8-Cl | 9-Cl | 245–248 |

Legend to Table 1:
1. 11-Chloro-7,8-dihydro-2,5-dioxo-2H,5H,9H-benzo[ij]pyrano[2,3-b]quinolizine-4-ol
2. 6-Ethyl-8-chloro-5,6-dihydro-2,5-dioxo-2H-pyrano[3,2-c]quinoline-4-ol
3. 7,8-Dihydro-11-methyl-2,5-dioxo-2H,5H,9H-benzo[ij]pyrano[2,3-b]quinolizine-4-ol
4. 7,8-Dihydro-11-methoxy-2,5-dioxo-2H,5H,9H-benzo[ij]-pyrano[2,3-b]quinolizine-4-ol
5. 11,12-Dichloro-7,8-dihydro-2,5-dioxo-2H,5H,9H-benzo-[ij]pyrano[2,3-b]quinolizine-4-ol
6. 6-Ethyl-9-chloro-5,6-dihydro-2,5-dioxo-2H-pyrano[3,2-c]quinoline-4-ol
7. 9-Chloro-5,6-dihydro-6-methyl-2,5-dioxo-2H-pyrano[3,2-c]quinoline-4-ol
8. 6-Ethyl-9-fluoro-5,6-dihydro-2,5-dioxo-2H-pyrano[3,2-c]quinoline-4-ol
9. 6-Ethyl-5,6-dihydro-2,5-dioxo-9-trifluoromethyl-2H-pyrano[3,2-c]quinoline-4-ol
10. 9-Ethoxycarbonyl-6-ethyl-5,6-dihydro-2,5-dioxo-2H-pyrano[3,2-c]quinoline-4-ol
11. 6-Ethyl-8,9-dichloro-5,6-dihydro-2,5-dioxo-2H-pyrano-[3,2-c]quinolin-4-ol

12.

11-Chloro-7,8-dihydro-3-nitro-2,5-dioxo-2H,5H,9H-benzo-[ij]pyrano[2,3-b]quinolizine-4-ol of the formula I 0.02 Mol 11-chloro-7,8-dihydro-2,5-dioxo-2H,5H,9H-benzo-[ij]pyrano[2,3-b]quinolizine-4-ol from Example 1 (6.1 g) are suspended in 12 ml of glacial acetic acid. The suspension is heated to 55° C. and 4 ml of nitric acid (d=1.40) is added dropwise, while stirring, in such a manner that the internal temperature does not exceed 65° C.

After the addition of the nitric acid stirring is continued for 5 minutes at 65° C. and the magma-like reaction batch is then cooled to a temperature in the range of from 0° to 10° C. During cooling, 10 ml of water are added and the precipitate is filtered off with suction, washed at first with a mixture of water and isopropanol (1:1), then with isopropanol and finally with petroleum ether. After drying, 6.4 g (91.8% of the theory) of a powdery residue are obtained. This residue is dissolved in 500 ml of acetonitrile. The crystals which have precipitated after cooling are filtered off with suction, washed and dried. 4.4 g (63.1% of the theory) of crystals are obtained; melting point (after recrystallization from dioxane): 242° to 244° C. (decomp.). After concentration of the acetonitrile phase, further 1.4 g (20.1% of the theory) of crystals are obtained; melting point (after recrystallization from dioxane) 242° to 244° C. (decomp.).

13.

9-Chlor-5,6-dihydro-6-methyl-3-nitro-2,5-dioxo-2H-pyrano[3,2-c]quinoline-4-ol of the formula I 0.02 Mole 9-chloro-5,6-dihydro-6-methyl-2,5-dioxo-2H-pyrano[3,2-c]quinoline-4-ol from Example 7 (5.6 g) is suspended in 25 ml of glacial acetic acid. 4 ml of nitric acid (d=1.40) are added dropwise at 25° C., while stirring, and the magma-like reaction batch is then heated for 60 minutes to 95° C. It is then cooled to 20° C. During cooling, 36 ml of a mixture of water and isopropanol (1:1) is added. The whole is then filtered. The filter residue is washed with water to neutrality and after washing with isopropanol and petroleum ether, it is dried. 5.5 g (85% of the theory) of a crystalline residue are obtained, the crystals of which have a melting point of 241°–243° C. (decomp.) after recrystallization from a mixture of isobutanol and dimethylformamide.

The compounds (Examples 12 to 23) prepared according to Examples 12 and 13 are compiled in Table 2 and likewise the salts prepared from them (Examples 25 to 35), the preparation of which is described in detail in Examples 24, 29, 31 and 34.

TABLE 2

| | Compounds of the formula I (Examples 12 to 23) and their salts (Examples 24 to 35) | | | | |
|---|---|---|---|---|---|
| Example | $R^1$ | $R^2$ | $R^3$ | $R^4$ | melting point °C. |
| 12 | —$CH_2$—$CH_2$—$CH_2$— | | H | 11-Cl | 242–244 (decomp.) |
| 13 | —$CH_3$ | H | H | 9-Cl | 241–243 (decomp.) |
| 14 | —$CH_2$—$CH_2$—$CH_2$— | | H | H | 300 (decomp.) |
| 15 | —$CH_2$—$CH_2$—$CH_2$— | | H | 11-$CH_3$ | 240–243 (decomp.) |
| 16 | —$CH_2$—$CH_2$—$CH_2$— | | H | 11-O—$CH_3$ | 246–248 (decomp.) |
| 17 | —$CH_2$—$CH_2$—$CH_2$— | | 11-Cl | 12-Cl | 322–325 (decomp.) |
| 18 | —$C_2H_5$ | H | H | 9-Cl | 230–232 (decomp.) |
| 19 | —$C_2H_5$ | H | H | 9-F | 204–206 |
| 20 | —$C_2H_5$ | H | H | 9-$CF_3$ | 196–199 |
| 21 | —$C_2H_5$ | H | H | 9-$CO_2C_2H_5$ | 215–217 (decomp.) |
| 22 | —$C_2H_5$ | H | 8-Cl | H | 242–244 (decomp.) |
| 23 | —$C_2H_5$ | H | 8-Cl | 9-Cl | 247–248 (decomp.) |

| Example | kind of salt | salt of compound of Example | melting point°C. |
|---|---|---|---|
| 24 | Na-salt | 12 | >330 (decomp.) |
| 24a | K-salt | 12 | 260–265 (decomp.) |
| 24b | Ethanolamine-salt | 12 | 212–215 |
| 24c | Diethanolamine-salt | 12 | 220–222 (decomp.) |
| 24d | Triethanolamine-salt | 12 | 200–205 |
| 24e | Tris(hydroxymethyl)-aminomethane-salt | 12 | 222–224 |
| 25 | Na-salt | 13 | >330 |

TABLE 2-continued

Compounds of the formula I (Examples 12 to 23) and their salts (Examples 24 to 35)

| | | | |
|---|---|---|---|
| 26 | Na-salt | 14 | >340 (decomp.) |
| 27 | Na-salt | 15 | >305 (decomp.) |
| 28 | Na-Salz | 16 | >260 (decomp.) |
| 29 | Ethanolamine-salt | 17 | 205-207 |
| 30 | Na-salt | 18 | >330 |
| 31 | Na-salt | 19 | 274-276 |
| 32 | Na-salt | 20 | >320 |
| 33 | Na-salt | 21 | 285-288 |
| 34 | Na-salt | 22 | 238-241 |
| 35 | Ethanolamine-salt | 23 | 212-214 |

Legend to Table 2:

| | |
|---|---|
| 12 + 24 + 24 a-e | 11-Chloro-7,8-dihydro-3-nitro-2,5-dioxo-2H,5H,9H-benzo[ij]pyrano[2,3-b]quinolizine-4-ol and its sodium, potassium-, ethanolamine-, diethanolamine-, triethanolamine- and tris-(hydroxymethyl)-aminomethane salt |
| 13 + 25 | 9-Chloro-5,6-dihydro-6-methyl-3-nitro-2,5-dioxo-2H-pyrano[3,2-c]quinoline-4-ol and its sodium salt |
| 14 + 26 | 7,8-Dihydro-3-nitro-2,5-dioxo-2H,5H,9H-benzo[ij]-pyrano[2,3-b]quinolizine-4-ol and its sodium salt |
| 15 + 27 | 7,8-Dihydro-11-methyl-3-nitro-2,5-dioxo-2H,5H,9H-benzo[ij]pyrano-[2,3-b]quinolizine-4-ol and its sodium salt |
| 16 + 28 | 7,8-Dihydro-11-methoxy-3-nitro-2,5-dioxo-2H,5H,9H-benzo[ij]pyrano[2,3-b]quinolizine-4-ol and its sodium salt |
| 17 + 29 | 11,12-Dichloro-7,8-dihydro-3-nitro-2,5-dioxo-2H-5H,9H-benzo[ij]-pyrano[2,3-b]quinolizine-4-ol and its ethanolamine salt |
| 18 + 30 | 6-Ethyl-9-chloro-5,6-dihydro-3-nitro-2,5-dioxo-2H-pyrano[3,2-c]-quinoline-4-ol and its sodium salt |
| 19 + 31 | 6-Ethyl-9-fluoro-5,6-dihydro-3-nitro-2,5-dioxo-2H-pyrano[3,2-c]quinoline-4-ol and its sodium salt |
| 20 + 32 | 6-Ethyl-5,6-dihydro-3-nitro-2,5-dioxo-9-trifluoromethyl-2H-pyrano[3,2-c]quinoline-4-ol and its sodium salt |
| 21 + 33 | 9-Ethoxycarbonyl-6-ethyl-5,6-dihydro-3-nitro-2,5-dioxo-2H-pyrano[3,2-c]quinoline-4-ol and its sodium salt |
| 22 + 34 | 6-Ethyl-8-chloro-5,6-dihydro-3-nitro-2,5-dioxo-2H-pyrano[3,2-c]quinoline-4-ol and its sodium salt |
| 23 + 35 | 6-Ethyl-8,9-dichloro-5,6-dihydro-3-nitro-2,5-dioxo-2H-pyrano[3,2-c]quinoline-4-ol and its ethanolamine salt |

PREPARATION OF SALTS

24.

11-Chloro-7,8-dihydro-3-nitro-2,5-dioxo-2H,5H,9H-benzo-[ij]pyrano[2,3-b]quinolizine-4-ol-sodium salt 0.1 Mole 11-Chloro-7,8-dihydro-3-nitro-2,5-dioxo-2H,5H,-9H-benzo[ij]pyrano[2,3-b]quinolizine-4-ol from Example 12 (34.9 g) are suspended in 1100 ml of water. At first, 20 ml of acetone are added, while stirring, and then such a quantity of 1 N-sodium hydroxide solution is added that the pH-value of the solution is 7.0. The reaction mixture is heated to 85° C. and filtered. The crystals which have separated from the filtrate upon cooling are filtered off with suction, washed with ethanol and petroleum ether and dried. 30.2 g (81% of the theory) of crystals are obtained; melting point (after recrystallization from water): 330° C. (decomp.).

29.

11,12-Dichloro-7,8-dihydro-3-nitro-2,5-dioxo-2H,5H,9H-benzo[ij]pyrano[2,3-b]-quinolizine-4-ol-ethanolamine salt 0.05 Mole of ethanolamine (3.05 g) is added dropwise, at the boiling temperature, to a suspension of 0.05 mole of 11,12-dichloro-7,8-dihydro-3-nitro-2,5-dioxo-2H,5H,9H-benzo[ij]pyrano[2,3-b]quinolizine-4-ol from Example 17 (19.2 g) in 900 ml of ethanol. The whole is refluxed for 15 minutes and cooled to room temperature. The precipitate that has formed is filtered off with suction, washed with ethanol and recrystallized from ethanol. 17.2 g (77.5% of the theory) of a light brown crystalline powder are obtained; melting point (after recrystallization from dimethylacetamide/methanol): 205°-207° C. (decomp.).

31.

6-Ethyl-9-fluoro-5,6-dihydro-3-nitro-2,5-dioxo-2H-pyrano[3,2-c]quinoline-4-ol-sodium salt 0.05 Mole of 6-ethyl-9-fluoro-5,6-dihydro-3-nitro-2,5-dioxo-2H-pyrano[3,2-c]quinoline-4-ol from Example 19 (16 g) are suspended in 250 ml of water. 15 ml of acetone are added and then such a quantity of 1 N-sodium hydrogenocarbonate solution is added that the pH-value of the solution is 7.0 to 7.5. After completion of the salt formation, the whole is heated to 70° to 80° C., filtered and the crystals that have formed upon cooling are filtered off with suction. They are washed with water and dried. 14.6 g (85% of the theory) of crystals are so obtained; melting point (after recrystallization from water): 274° to 276° C.

34.

6-Ethyl-8-chloro-5,6-dihydro-3-nitro-2,5-dioxo-2H-pyrano[3,2-c]quinoline-4-ol-sodium salt 0.05 Mol of 6-ethyl-8-chloro-5,6-dihydro-3-nitro-2,5-dioxo-2H-pyrano[3,2-c]quinoline-4-ol from Example 22 (16.8 g) are dissolved in 75 ml of dimethylacetamide. This solution is allowed to drop, while stirring, into a suspension of 1.5 g of a 80% strength sodium hydride-paraffin suspension (Merck) in 25 ml of dimethylacetamide. Upon termination of the evolution of hydrogen, the whole is further stirred for 15 minutes at 40° to 50° C. It is then allowed to cool, filtered at 25° C. and the filtrate is combined, while stirring, with 750 ml of a mixture of methylethyl-ketone and methanol (2:1). It is shortly refluxed and cooled, so that the sodium salt precipitates in crystalline and analytically pure form. The crystals are filtered off with suction, washed and dried. 15.4 g (86% of the theory) of crystals are obtained; melting point 238°–241° C.

PHARMACOLOGICAL TESTS AND RESULTS

The compounds of the invention of the formula I and their salts have strong antiallergic properties and are well tolerated on intravenous as well as oral administration in the models of passive cutaneous anaphylaxis (P C A) to rats.

According to the method described by J. Goose and A. M. J. N. Blair, Immunology 16, 749 (1969) a P C A is made ready on Sprague-Dawley rats by intracutaneous administration of homologous antiserum, 0.1 ml of a dilution of 1:16 and 1:32 in both flanks. The antiserum is directed against ovalbumine and is induced in rats by combined administration of ovalbumine with Bordetella pertussis as adjuvant and boostering with Nippostrongylus larvae. 72 hours after the intracutaneous administration of the antiserum, the intravenous injection of the antigen consisting of a mixture of each time 25 mg/kg of ovalbumine and Evans blue is effected, in order to trigger the cutaneous anaphylactic reaction. The compounds of the formula I or their salts are administered, if intravenously, directly before the injection of the ovalbumine-dyestuff mixture and if administered orally, 30 minutes before the administration of the ovalbumine-dyestuff mixture. 10 Minutes after the ovalbumine-dyestuff injection, the animals are sacrificed and the diameter of spreading of the dyestuff is measured in the hypodermis.

As comparative substance, the standard preparation di- sodium-chromoglycate (DSCG) is used.

The results of the passive cutaneous anaphylaxis test (PCA) are compiled in the following Tables 3 and 4.

TABLE 3

| Compound of Example | n | Dose in mg/kg | % Inhibition against control (Dilution 1:16) |
|---|---|---|---|
| 24 (12) | 6 | 0.1 | 12 |
| | | 0.3 | 50 |
| | | 1.0 | 89 |
| | | 3.0 | 100 |
| 25 (13) | 5 | 0.01 | 44 |
| | | 0.03 | 67 |
| | | 0.1 | 100 |
| 30 (18) | 5 | 0.03 | 50 |
| | | 0.1 | 88 |
| | | 0.3 | 100 |
| 31 (19) | 5 | 0.01 | 27 |

Inhibition of PCA in rats on intravenous treatment

TABLE 3-continued

| Compound of Example | n | Dose in mg/kg | % Inhibition against control (Dilution 1:16) |
|---|---|---|---|
| | | 0.03 | 60 |
| | | 0.1 | 80 |
| | | 0.3 | 87 |
| | | 3.0 | 100 |
| 32 (20) | 5 | 0.03 | 19 |
| | | 0.1 | 69 |
| 32 (20) | 5 | 0.3 | 75 |
| | | 3.0 | 100 |
| 35 (23) | 5 | 0.1 | 20 |
| | | 0.3 | 53 |
| | | 1.0 | 73 |
| | | 30.0 | 100 |
| DSCG as comparison | 6 | 0.1 | 9 |
| | | 0.3 | 34 |
| | | 1.0 | 71 |

Inhibition of PCA in rats on intravenous treatment n designates the number of animals used for each dose.

The numbers in brackets in the first column designate the number of the Example of the respective basic compound.

TABLE 4

| Compound of Example | n | Dose in mg/kg | % Inhibition against control with dilution of th antiserum | |
|---|---|---|---|---|
| | | | 1:16 | 1:32 |
| 24 | 6 | 0.3 | 22 | 27 |
| | | 1.0 | 50 | 73 |
| | | 3.0 | 44 | 73 |
| | | 10.0 | 44 | 73 |
| DSCG as comparison | 6 | 10.0 | 0 | 0 |
| | | 30.0 | 5 | 0 |

Inhibition of PCA in rats on oral treatment n designates the number of animals used for each dose.

As evident from Tables 3 and 4, the compounds of the invention show after parenteral administration an essentially stronger antianaphylactic action than the comparative preparation DSCG. An advantage of the compounds which is especially important for the therapy, over the orally inactive DSCG, is that they are also highly active when administered orally.

What is claimed is:

1. A compound of the formula I

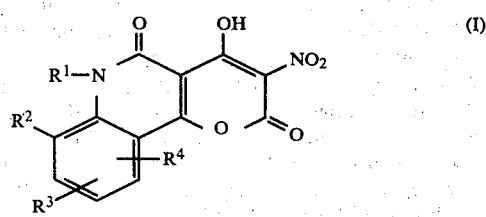

and a physiologically tolerated salt thereof, wherein
$R^1$ is hydrogen or alkyl having 1 to 4 carbon atoms,
$R^2$ is hydrogen or a radical selected from the group consisting of alkyl, alkoxy or haloalkyl each having up to 3 carbon atoms, and halogen atoms, or
$R^1$ and $R^2$ together form an ethylene or propylene group,
$R^3$ and $R^4$, are, independently from each other, hydrogen or a radical selected from the group consisting of alkyl and alkoxy each having up to 3 carbon atoms being unsubstituted or at least partially substituted, with the same or different halogen atoms;

halogen atoms; or alkoxycarbonyl groups having up to 3 carbon atoms in the alkyl radical.

2. A compound as defined in claim 1 and a physiologically tolerated salt thereof wherein
R$^1$ and R$^2$ together form a propylene group and
R$^3$ and R$^4$ are the same or different and are hydrogen or one of the radicals selected from the group consisting of alkyl, alkoxy, each having 2 carbon atoms, or halogen or the CF$_3$ group.

3. A compound as defined in claim 1 and a physiologically tolerated salt thereof wherein
R$^1$ is hydrogen or alkyl having up to 3 carbon atoms,
R$^2$ is hydrogen, and
R$^3$ and R$^4$ are identical or different, and are hydrogen or a radical selected from the group consisting of alkyl or alkoxy each having up to 2 carbon atoms, alkoxy-carbonyl having up to 3 carbon atoms in the alkyl radical, or halogen or the CF$_3$ group.

4. A compound as defined in claim 1 of the formula II

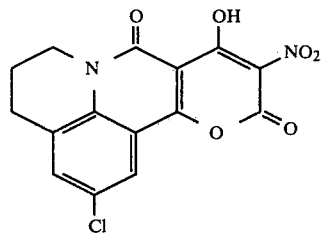

and a physiologically tolerated salt thereof.

5. A medicinal composition comprising an effective amount of a compound as defined in any one of claims 1, 2, 3, or 4 or of a physiologically tolerated salt thereof, for the treatment and/or prophylaxis of allergic diseases and an inert carrier therefor.

* * * * *